US009228898B2

United States Patent
Kiani et al.

(10) Patent No.: US 9,228,898 B2
(45) Date of Patent: Jan. 5, 2016

(54) SCALABLE SPECTROSCOPIC DETECTION AND MEASUREMENT

(75) Inventors: Sepehr Kiani, Cambridge, MA (US); Peter Lewis Stokes, Cambridge, MA (US); David H. Tracy, Cambridge, MA (US)

(73) Assignee: GNUBIO, INC., Cambridge, MA (US)

( * ) Notice: Subject to any disclaimer, the term of this patent is extended or adjusted under 35 U.S.C. 154(b) by 0 days.

(21) Appl. No.: 14/008,964

(22) PCT Filed: Mar. 27, 2012

(86) PCT No.: PCT/US2012/030716
§ 371 (c)(1),
(2), (4) Date: Jan. 17, 2014

(87) PCT Pub. No.: WO2012/135201
PCT Pub. Date: Oct. 4, 2012

(65) Prior Publication Data
US 2014/0198313 A1      Jul. 17, 2014

Related U.S. Application Data

(60) Provisional application No. 61/469,889, filed on Mar. 31, 2011.

(51) Int. Cl.
*G01J 3/28* (2006.01)
*G01J 3/42* (2006.01)
(Continued)

(52) U.S. Cl.
CPC .. *G01J 3/42* (2013.01); *G01J 3/021* (2013.01); *G01J 3/0208* (2013.01); *G01J 3/0216* (2013.01);
(Continued)

(58) Field of Classification Search
CPC ................. G01J 3/02; G01J 3/28; G01J 3/18; G01J 3/2803; G01J 3/2823; G01J 3/10
USPC .................................................. 356/300–334
See application file for complete search history.

(56) References Cited

U.S. PATENT DOCUMENTS

| 2,975,669 A | 3/1961 | Jarrell et al. |
| 5,159,199 A | 10/1992 | LaBaw |

(Continued)

FOREIGN PATENT DOCUMENTS

| CN | 101023331 A | 8/2007 |
| CN | 101473201 A | 7/2009 |

(Continued)

OTHER PUBLICATIONS

Extended European Search Report mailed Aug. 20, 2014, from European Application No. 12765764.1 (12 pages).
(Continued)

*Primary Examiner* — Abdullahi Nur
(74) *Attorney, Agent, or Firm* — Kilpatrick Townsend & Stockton LLP

(57) ABSTRACT

The present invention generally pertains to a system, method and kit for the detection and measurement of spectroscopic properties of light from a sample, or the scalable detection and measurement of spectroscopic properties of light from each sample present among multiple samples, simultaneously, wherein the system comprises: an optical train comprising a dispersing element; and an image sensor. The light detected and measured may comprise light scattered from a sample, emitted as chemiluminescence by a chemical process within a sample, selectively absorbed by a sample, or emitted as fluorescence from a sample following excitation.

31 Claims, 9 Drawing Sheets

(51) Int. Cl.
  *G01J 3/02* (2006.01)
  *G01J 3/06* (2006.01)
  *G01N 21/64* (2006.01)
  *G01N 15/14* (2006.01)
  *G01J 3/44* (2006.01)
  *G01J 3/08* (2006.01)
  *G01J 3/10* (2006.01)
  *G01J 3/14* (2006.01)
  *G01J 3/18* (2006.01)

(52) U.S. Cl.
  CPC ............ *G01J 3/0248* (2013.01); *G01J 3/0291* (2013.01); *G01J 3/06* (2013.01); *G01J 3/08* (2013.01); *G01J 3/10* (2013.01); *G01J 3/14* (2013.01); *G01J 3/18* (2013.01); *G01J 3/2803* (2013.01); *G01J 3/44* (2013.01); *G01J 3/4406* (2013.01); *G01N 15/1434* (2013.01); *G01N 15/1459* (2013.01); *G01N 15/1484* (2013.01); *G01N 21/6456* (2013.01)

(56) References Cited

U.S. PATENT DOCUMENTS

| | | | |
|---|---|---|---|
| 5,206,701 | A | 4/1993 | Taylor et al. |
| 5,434,629 | A | 7/1995 | Pearson et al. |
| 5,862,001 | A | 1/1999 | Sigler |
| 6,017,434 | A | 1/2000 | Simpson et al. |
| 6,043,881 | A | 3/2000 | Wegrzyn et al. |
| 6,875,973 | B2 * | 4/2005 | Ortyn et al. ............. 250/201.3 |
| 8,047,829 | B1 | 11/2011 | Sommer et al. |
| 8,528,589 | B2 | 9/2013 | Miller et al. |
| 8,535,889 | B2 | 9/2013 | Larson et al. |
| 2002/0009741 | A1 | 1/2002 | Simpson et al. |
| 2003/0127609 | A1 | 7/2003 | El-Hage et al. |
| 2003/0193589 | A1 | 10/2003 | Lareau et al. |
| 2004/0197816 | A1 | 10/2004 | Empedocles et al. |
| 2005/0237403 | A1 | 10/2005 | Baykal et al. |
| 2006/0066837 | A1 * | 3/2006 | Ortyn et al. ................. 356/73 |
| 2006/0258942 | A1 | 11/2006 | Van Beek et al. |
| 2007/0242111 | A1 | 10/2007 | Pamula et al. |
| 2008/0014589 | A1 | 1/2008 | Link et al. |
| 2009/0059220 | A1 | 3/2009 | Tuschel et al. |
| 2009/0310132 | A1 | 12/2009 | Bennett et al. |
| 2011/0151578 | A1 | 6/2011 | Abate et al. |
| 2011/0218123 | A1 | 9/2011 | Weitz et al. |
| 2011/0250597 | A1 | 10/2011 | Larson et al. |
| 2011/0267457 | A1 | 11/2011 | Weitz et al. |
| 2012/0015822 | A1 | 1/2012 | Weitz et al. |
| 2012/0132288 | A1 | 5/2012 | Weitz et al. |
| 2012/0219947 | A1 | 8/2012 | Yurkovetsky et al. |
| 2012/0220494 | A1 | 8/2012 | Samuels et al. |
| 2012/0222748 | A1 | 9/2012 | Weitz et al. |
| 2012/0309002 | A1 | 12/2012 | Link |
| 2015/0024945 | A1 | 1/2015 | Healy |

FOREIGN PATENT DOCUMENTS

| | | |
|---|---|---|
| EP | 2364774 A2 | 9/2011 |
| EP | 2662135 A2 | 11/2013 |
| WO | 2007/081385 A2 | 7/2007 |
| WO | 2007/081387 A1 | 7/2007 |
| WO | 2012/078710 A1 | 6/2012 |
| WO | 2012/135201 A1 | 10/2012 |
| WO | 2012/135259 A1 | 10/2012 |
| WO | 2012/135327 A1 | 10/2012 |
| WO | 2013095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014/117088 A1 | 7/2014 |
| WO | 2014/176599 A1 | 10/2014 |

OTHER PUBLICATIONS

International Search Report and Written Opinion mailed Jul. 13, 2012, from PCT Application No. PCT/US2012/030716 (13 pages).
International Preliminary Report on Patentability mailed Oct. 10, 2013, from PCT Application No. PCT/US2012/030716 (12 pages).
Marras, Salvatore A.E., "Selection of Fluorophore and Quencher Pairs for Fluorescent Nucleic Acid Hybridization Probes," *Methods in Molecular Biology: Fluorescent Energy Transfer Nucleic Acid Probes: Designs and Protocols*, 2006, vol. 335, pp. 3-16, Editor V. Didenko, Publisher Humana Press Inc., New Jersey, USA.
Han, Mingyong et al., "Quantum-dot-tagged Microbeads for Multiplexed Optical Coding of Biomolecules," Nature Biotechnology, Jul. 2001, vol. 19, pp. 631-635.
U.S. Appl. No. 14/289,982, filed May 29, 2014.
U.S. Appl. No. 14/470,860, filed Aug. 27, 2014.
U.S. Appl. No. 14/502,948, filed Sep. 30, 2014.
International Appl. No. PCT/US2014/035730, filed Apr. 28, 2014, in the name of GnuBio, Inc.
Examination Report mailed Dec. 26, 2014, from Singaporean Application No. 2013068820 (12 pages).
First Examination Report mailed Jan. 8, 2015, from Australian Application No. 2012236748 (3 pages).
Office Action and Search Report mailed Feb. 28, 2015, from Chinese Application No. 201280018232.9 (14 pages).
Written Opinion mailed Jun. 23, 2015, from Singaporean Application No. 2013068820 (13 pages).

* cited by examiner

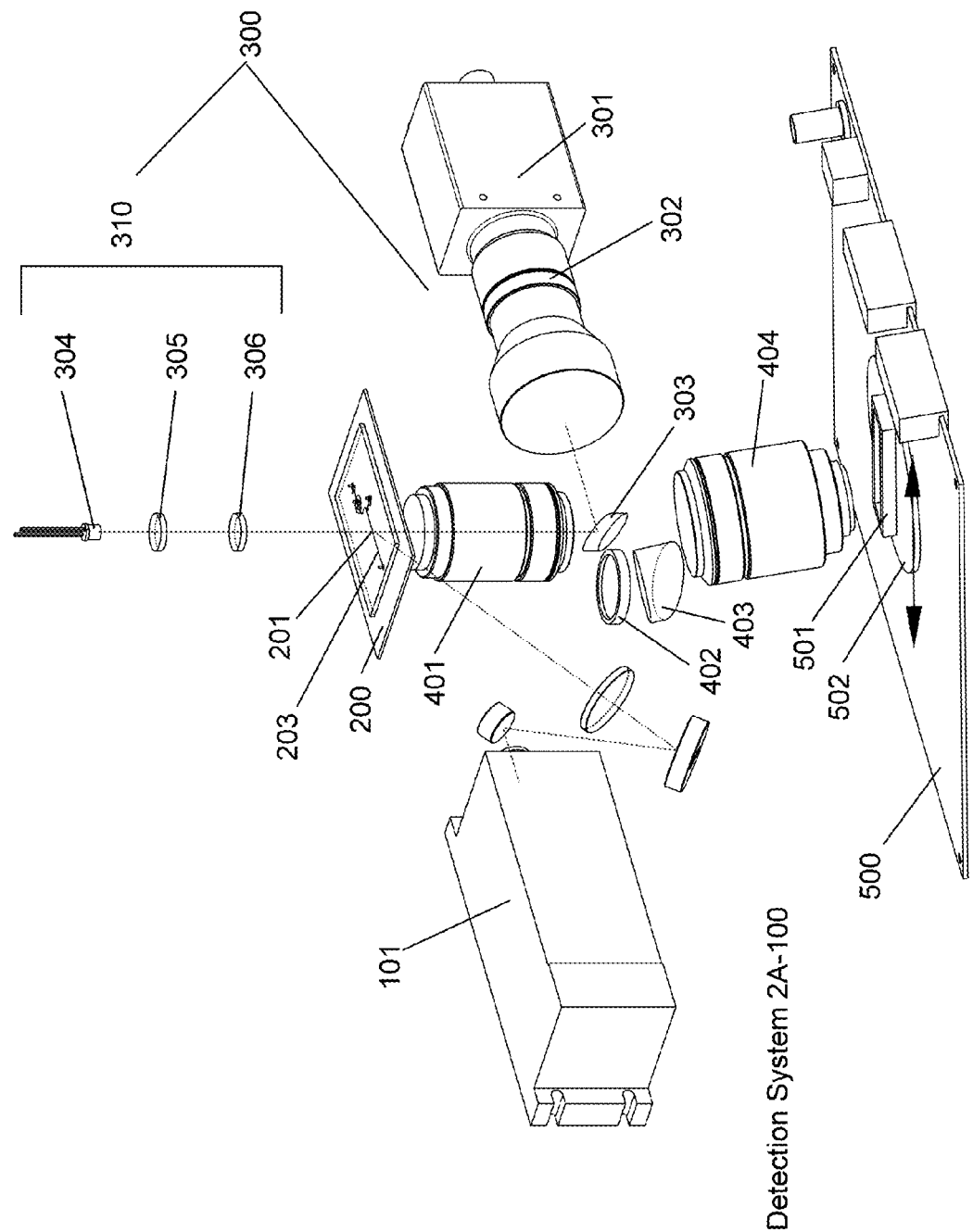

Detection System 4A-100

Detection System 4B-100

SCALABLE SPECTROSCOPIC DETECTION AND MEASUREMENT

RELATED APPLICATIONS AND INCORPORATION BY REFERENCE

This application is a national phase application under 35 USC§371 of PCT Application No. PCT/US2012/030716 filed Mar. 27, 2012, which claims the benefit of priority to U.S. provisional patent application Ser. No. 61/469,889 filed Mar. 31, 2011, the teaching and contents of which are hereby incorporated by reference.

The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention is in the technical field of optics. More particularly, the present invention relates to a system, method and kit for the detection and measurement of spectroscopic properties of a sample.

BACKGROUND OF THE INVENTION

Many chemical and biochemical detection methods have been developed that require costly and sensitive reagents. Applications for these detection methods are sought where the detection device must be compact. These are some motivators for the development of microfluidic devices, which encompass analytical systems where reactions and detections are performed on fluids or suspended solids carried in microscale channels. The very small amounts of materials used for these reactions and detections allows for, among other things, cost-effective analysis and the use of instrumentation in settings where space is limited.

Many detection methods involve determining spectroscopic properties of light from a sample, where the light may be scattered from a sample, or emitted as chemiluminescence by a chemical process within a sample, or transmitted through a sample, or selectively absorbed by a sample, or emitted as fluorescence from a sample following excitation.

Photomultiplier tubes (PMTs) are commonly used to detect, for example, fluorescent signals. Known systems employing PMTs are constrained by the inability of a PMT to discern the frequency of incident light. To provide this sensitivity, the system must also incorporate an optical filter ahead of the PMT, chosen to select only the particular wavelength of interest. Systems using PMTs for detection of multiple colors require a means to distribute the observed light among several PMTs, one for each discrete color to be detected, each of which must have its own particular filter. A PMT based system for measuring emissions from several samples at once would have to duplicate all of this distribution, filtering and detection hardware for each sample to be observed. Additionally, any change in the colors of light to be detected would require the replacement of the corresponding filters.

Accordingly, there is a need for a system that is able to efficiently perform a large number of high-speed, discrete measurements of arbitrary spectroscopic properties in very small targets, as is provided by the following invention.

Citation or identification of any document in this application is not an admission that such document is available as prior art to the present invention.

SUMMARY OF THE INVENTION

The present invention generally pertains to a system for the detection and measurement of spectroscopic properties of light from a sample, or the scalable detection and measurement of spectroscopic properties of light from each sample present among multiple samples, simultaneously, wherein the system comprises: an optical train comprising a dispersing element; and an image sensor. The light detected and measured may comprise light scattered from a sample following illumination of a sample; emitted as chemiluminescence by a chemical process within a sample; selectively absorbed by a sample following direction of a broadband light source at a sample; or emitted as fluorescence from a sample following excitation. The light from each sample may be spectrally dispersed by the dispersing element and the spectroscopic properties of the light may be measured over time on the image sensor as a function of relative motion between a particular sample and the image sensor. Depending on the application, the sample may comprise a single-phase flow, the composition of which may vary with time; discrete targets including, but not limited to, beads or cells; or droplets. In one embodiment, one or more samples of interest may be present in an emulsion. In another embodiment, one or more samples may be present in an emulsion within a microfluidic device.

The present invention also pertains to a method for the detection and measurement of spectroscopic properties of light from a sample, or the scalable detection and measurement of spectroscopic properties of light from each sample present among multiple samples, simultaneously, wherein the system may comprise: an optical train comprising a dispersing element; and an image sensor. The light detected and measured may comprise light scattered from a sample following illumination of a sample; emitted as chemiluminescence by a chemical process within a sample; selectively absorbed by a sample following direction of a broadband light source at a sample; or emitted as fluorescence from a sample following excitation. The light from each sample may be spectrally dispersed by the dispersing element and the spectroscopic properties of the light may be measured over time on the image sensor as a function of relative motion between a particular sample and the image sensor. Depending on the application, the sample may comprise a single-phase flow, the composition of which may vary with time; discrete targets including, but not limited to, beads or cells; or droplets. In one embodiment, one or more samples of interest may be present in an emulsion. In another embodiment, one or more samples may be present in an emulsion within a microfluidic device.

The present invention also pertains to a kit containing the system and reagents for the detection and measurement of spectroscopic properties of light from a sample, or the scalable detection and measurement of spectroscopic properties of light from each sample present among multiple samples, simultaneously, wherein the system may comprise: an optical train comprising a dispersing element; and an image sensor. The light detected and measured comprises light scattered from a sample following illumination of a sample; emitted as chemiluminescence by a chemical process within a sample; selectively absorbed by a sample following direction of a broadband light source at a sample; or emitted as fluorescence from a sample following excitation. The light from each sample may be spectrally dispersed by the dispersing element and the spectroscopic properties of the light may be measured over time on the image sensor as a function of relative motion between a particular sample and the image sensor. Depending on the application, the sample may comprise a single-phase flow, the composition of which may vary with time; discrete targets including, but not limited to, beads or cells; or droplets. In one embodiment, one or more samples of interest may be present in an emulsion. In another embodiment, one or more samples may be present in an emulsion within a microfluidic device.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 2A is a representative illustration of a monitor camera system adapted to the system of FIG. 1, employing trans-illumination of the sample.

DETAILED DESCRIPTION OF THE INVENTION

Figure 1:
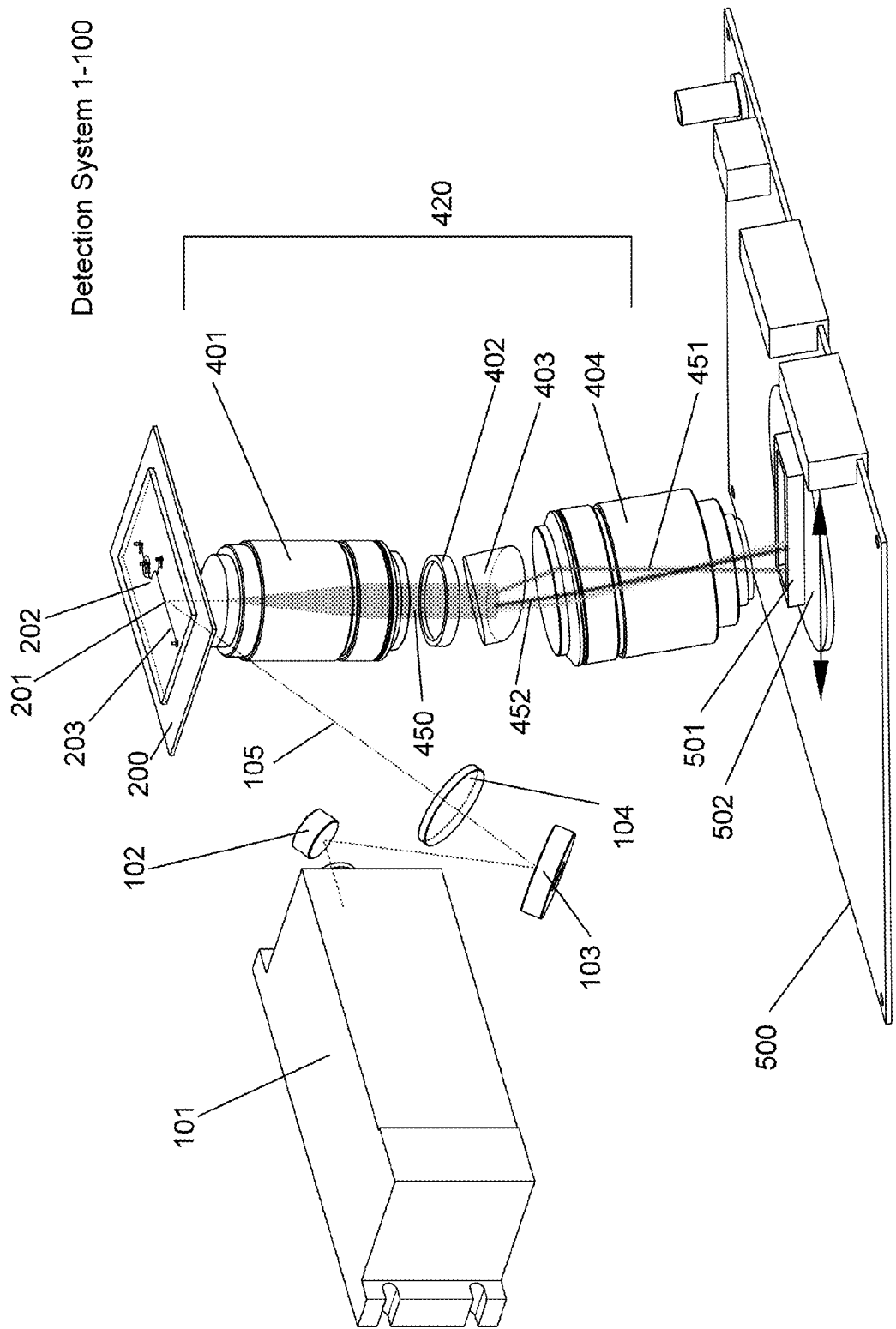
FIG. 1 is a representative illustration of an embodiment of the system of the present invention.

The present invention generally pertains to a system for the detection and measurement of spectroscopic properties of light from a sample, or the scalable detection and measurement of spectroscopic properties of light from each sample present among multiple samples, simultaneously, wherein the system comprises: an optical train comprising a dispersing element; and an image sensor. The light detected and measured may comprise light scattered from a sample following illumination of the sample; emitted as chemiluminescence by a chemical process within a sample; selectively absorbed by a sample following direction of a broadband light source at the sample; or emitted as fluorescence from a sample following excitation. Depending on the application, the sample may comprise a single-phase flow, the composition of which may vary with time; discrete targets including, but not limited to, beads or cells; or droplets.

An "optical train", as used herein, means a functional grouping of one or more optical elements employed to effect one or more particular transformations of gathered light, such as collimation, magnification, distortion, filtering, or dispersion.

An "image sensor", as used herein, means a single- or multi-element light-sensitive transducer capable of detecting a spatial pattern of light incident on a plane and converting said pattern into output signals representative of said pattern, with said detection and conversion being carried out repetitively at regular time interval.

A "sample(s)", "one or more samples", or "sample(s) of interest" are terms used interchangeably in singular or plural form and are not intended to be limited to any particular quantity.

In one embodiment of the system of the present invention, the sample is a single-phase flow, the composition of which may vary with time.

In another embodiment of the system of the present invention, the sample is a discrete target, including but not limited to, a bead or cell. A "bead", as used herein, refers to a fine particle used as a substrate or matrix for reactive substances and/or identifying labels in a diagnostic application, including beads of magnetic material, silica, or polymers including, but not limited to, polystyrene. A "cell" or "cells" as used herein, refer to any eukaryotic or prokaryotic cells, including but not limited, to cells selected from humans, animals, plants, fungi, bacteria, viruses, protozoa, yeasts, molds, algae, rickettsia, and prions.

In yet another embodiment of the system of the present invention, the sample is a droplet. A "droplet", as used herein, means an isolated aqueous or lipophilic phase within a continuous phase having any shape, for example but not limited to, cylindrical, spherical and ellipsoidal, as well as flattened, stretched or irregular shapes and so on.

In one embodiment of the system of the present invention, the one or more samples are present in an emulsion. An "emulsion", as used herein, is a stable mixture of at least two immiscible or partially immiscible liquids. In general, immiscible liquids tend to separate into two distinct phases. Accordingly, a surfactant may be added to stabilize the emulsion by reducing surface tension between the at least two immiscible or partially immiscible liquids and/or to stabilize the interface. For example, an emulsion may comprise a plurality of aqueous droplets in an immiscible oil, such as fluorocarbon oil, silicon oil or hydrocarbon oil (including but not limited to, petroleum and mineral oil) where the droplet size ranges from about 0.5 to about 5000 microns in diameter.

In another embodiment, the samples are present in an emulsion within a microfluidic device. A "microfluidic device", as used herein, is a device that enables a means of effecting a deterministic function on liquid or gas fluids at small scales typically measured in volumes such as, for example, milliliter (mL), microliter (μL), nanoliter (nL), picoliter (pL), or femtoliter (fL) volumes and/or by physical scale such as millimeter (mm), micrometer (μm) (also referred to as "micron"), nanometer (nm), picometer (pm), or femtometer (fm). Functions may include mixing, splitting, sorting, heating, and so forth. Microfluidic devices may comprise microfluidic channels as a means for transferring fluids or samples from one point to another and are typically of uniform cross section in the mm, μm or nm scale.

In one embodiment of the invention, the system comprises one or more microfluidic devices continuous with one or more microfluidic channels in conjunction with an optical train and an image sensor. In one aspect of this embodiment, one or more samples are present within an emulsion and flow through the one or more microfluidic devices and the one or more microfluidic channels. In any aspect, while flowing through the one or more microfluidic channels, the one or more samples are detected and analyzed by the optical train and the image sensor present in the system. The one or more samples flow by being acted upon by a source of positive or negative pressure, e.g., a pressurized or evacuated air reservoir, or a syringe pump, gravity or centripetal forces, wherein the pressure source comprises any fluid or combinations of fluids, including but not limited to any gas or combination of gases (e.g., air, nitrogen, carbon dioxide, argon, and so forth) and any liquid or combinations of liquids (e.g., water, buffer, oil, and so forth), such that the one or more samples flow or stream through the one or more microfluidic devices and the one or more microfluidic channels and are herein referred to as "flowing sample(s)" or "streaming sample(s)".

In one embodiment of the system of the present invention, the flowing sample(s) in the one or more microfluidic channels may comprise a continuous phase liquid whose spectroscopic properties are to be measured. In another embodiment, the flowing sample(s) in the one or more microfluidic channels may comprise a suspension of cells or beads carried in a fluid. In another embodiment, the flowing sample(s) are illuminated with a light source, resulting in scatter comprising characteristic colors of light. In yet another embodiment, the flowing sample(s) selectively absorb characteristic colors of light when light from a light source passes through them. In yet another embodiment, the flowing sample(s) emit light by chemiluminescence.

A wide variety of methods and materials exists and will be known and appreciated by one of skill in the art for construction of microfluidic channels and networks thereof, such as those described, for example, in U.S. Pat. No. 8,047,829 and U.S. Patent Application Publication No. 20080014589, each of which is incorporated herein by reference in its entirety. For example, the microfluidic channel may be constructed using simple tubing, but may further involve sealing the surface of one slab comprising open channels to a second flat slab. Materials into which microfluidic channels may be formed include silicon, glass, silicones such as polydimethylsiloxane (PDMS), and plastics such as poly(methyl-methacrylate) (known as PMMA or "acrylic"), cyclic olefin polymer (COP), and cyclic olefin copolymer (COC). The same materials can also be used for the second sealing slab. Compatible combinations of materials for the two slabs depend on the method employed to seal them together. The microfluidic channel may be encased as necessary in an optically clear material to allow for optical excitation (resulting in, e.g., fluorescence) or illumination (resulting in, e.g., selective absorption) of a sample as necessary, and to allow for optical detection of spectroscopic properties of light from a sample, as the sample is flowing through the microfluidic channel. Preferred examples of such optically clear materials that exhibit high optical clarity and low autofluorescence include, but are not limited to, borosilicate glass (e.g., SCHOTT BOROFLOAT® glass (Schott North America, Elmsford N.Y.)) and cyclo-olefin polymers (COP) (e.g., ZEONOR® (Zeon Chemicals LP, Louisville Ky.)).

In one embodiment of the present invention, the system provides for the detection and measurement of wavelength and intensity of fluorescence emitted by one or more samples following excitation, wherein fluorescently-labeled samples are identified by combinations of different colors and intensities of fluorescent material. The fluorescent material is referred to as a "fluorescent label" or "fluorophore" or "fluorescent dye", each of which as used herein when describing a "fluorescently-labeled sample" may be a fluorescent molecule, a fluorescent semiconductor nanoparticle (referred to as a "quantum dot"), or a chelated lanthanide or lanthanoid, having the ability to absorb energy from light of a specific wavelength, and then emit this energy as fluorescence in another specific wavelength characteristic for the particular molecule or quantum dot. In this manner, the fluorophore will facilitate the final assay readout indicating the presence or absence of a particular target of interest in the sample. In one aspect of this embodiment, a fluorescently-labeled sample is present within a droplet. In another aspect, a fluorescently-labeled sample is present within or coated on a discrete particle. In one example, the discrete particle is a cell. In another example, the discrete particle is a bead. In another aspect, a fluorescently-labeled sample is present within a single-phase flow.

The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. *Fluorescent Energy Transfer Nucleic Acid Probes: Designs and Protocols* (Methods in Molecular Biology, vol. 335). New Jersey: Humana Press Inc., pp. 3-16. Examples of fluorophores that may be employed in the present invention include, but are not limited to, those described by Marras 2006 and further described herein below. One of skill in the art will appreciate the various fluorescent dyes that may serve as fluorescent labels and that may be employed in the present invention and which are available from various commercial vendors.

Examples of fluorescent dyes that may be employed in the present invention include, but are not limited to, the following: fluorescein and derivatives thereof (e.g., fluorescein isothianate (FITC), carboxyfluorescein (FAM), tetrachlorofluorescein (TET), 2',7'-difluorofluorescein (Oregon Green® 488), Oregon Green® 514 carboxylic acid, and a fluorescein with chloro and methoxy substituents (JOE and 6-JOE)); rhodamine derivatives (e.g., tetramethyl rhodamine (TAMRA), tetramethyl rhodamine iso-thiocyanate (TRITC), tetramethylrhodamine (TMR), carboxy-X-rhodamine (ROX), Texas Red (a mixture of isomeric sulfonyl chlorides and sulforhodamine; Invitrogen™) and Texas Red-X (Texas Red succinimidyl ester, which contains an additional seven-atom aminohexanoyl spacer ("X") between the fluorophore and its reactive group; Invitrogen™), and Rhodamine X); cyanine (Cy) dyes (e.g., Cy3, Cy5 and Cy5.5) and cyanine derivatives (e.g., indocarbocyanine (Quasar® 570, Quasar® 670 and Quasar® 705), Oregon Green® isothiocyanate, and eosin isothiocyanate (EITC)); N-hydroxysuccinimidyl 1-pyrenebutyrate (PYB); N-hydroxysuccinimidyl 1-pyrenesulfonate (PYS); (5-(2'-aminoethyl)aminonaphthalene (EDANS); CAL Fluor® Gold 540, CAL Fluor® Orange 560, Fluor® Red 590, CAL Fluor® Red 610, and CAL Fluor® Red 635 (proprietary fluorophores available from Biosearch Technologies, Inc.); VIGO; HEX® (a 6-isomer phosphoramidite); and NED®.

The particular quantum dot (QD) employed is not critical to the present invention. Quantum dots are known in the art and are described, for example, by Han et al., "Quantum-dot-tagged Microbeads for Multiplexed Optical Coding of Biomolecules", *Nat Biotechnol* (July 2001) vol. 19, pp. 631-635. One of skill in the art will appreciate the various quantum dots that may serve as fluorescent labels and that can be employed in the present invention and which are available from various commercial vendors. Examples of quantum dots (QDs) that may be employed in the present invention include, but are not limited to, the following: cadmium selenide (CdSe) quantum dot nanoparticles (e.g., CdSe Quantum Dot Cores, 480-640 nm emission spectra, Sigma-Aldrich®); cadmium sulfide (CdS) quantum dot nanoparticles (e.g., CdS Quantum Dot Cores, 380-480 nm emission spectra, Sigma-Aldrich®); zinc sulfide-capped cadmium selenide (ZnS-capped CdSe) nanocrystals (e.g., CdSe/ZnS Lumidots™ and CdSe/ZnS NanoDots™, 480-640 nm emission spectra, Sigma-Aldrich®); and cadmium-free quantum dots (e.g., CFQD™, 400-650 nm emission spectra, Sigma-Aldrich®).

The particular chelated lanthanide or lanthanoid employed is not critical to the present invention. Lanthanides and lanthanoids are known in the art to comprise the fifteen metallic chemical elements with atomic numbers 57 through 71, from lanthanum (La) through lutetium (Lu). Examples of lanthanides or lanthanoids in chelated form that may be employed in the present invention include, but are not limited to, the following: lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu).

In another embodiment of the present invention, the system provides for the detection and measurement of light emitted as chemiluminescence by one or more chemical processes in a sample. In one aspect of this embodiment, a chemiluminescent sample is present within a droplet. In another aspect, a chemiluminescent sample is present within or coated on a discrete particle. In one example, the discrete particle is a cell. In another example, the discrete particle is a bead. In another aspect, a chemiluminescent sample is present within a single-phase flow.

Typical examples of chemiluminescent reactions involve the catalyzed formation of unstable organic peroxides, which emit single photons as they decay to lower-energy states. A common example of a chemiluminescent compound is luminol (CAS 521-31-3), which produces a chemiluminescent reaction in the presence of an oxidizer (for example, hydrogen peroxide catalyzed with potassium ferracyanide to form oxygen) and a hydroxide salt. Examples in the art of the diagnostic application of chemiluminescence include, but are not limited to, those in which the concentration of an enzyme, which acts as a catalyst to the chemiluminescent reaction, is to be measured, as with the use of luminol to detect hemoglobin, and those in which the chemiluminescent compound is labeled directly to a reagent, as in immunoassays employing chemiluminescent complementary binding partners. One of skill in the art will know and appreciate these and many other examples of chemiluminescent reactions in the art, including those described in, for example, K. and R. Van Dyke eds. 1990, *Luminescence Immunoassay and Molecular Applications*, Boca Raton: CRC Press.

In yet another embodiment of the present invention, the system provides for the detection and measurement of scattered light comprising characteristic colors of light following illumination of a sample, for example but not limited to, by a broadband light source. In one aspect of this embodiment, a sample is present within a droplet. In another aspect, a sample is present within or coated on a discrete particle. In one example, the discrete particle is a cell. In another example, the discrete particle is a bead. In another aspect, a sample is present within a single-phase flow.

In still another embodiment of the present invention, the system provides for the detection and measurement of light transmitted through a sample as the sample absorbs certain characteristic colors or wavelengths of light while other colors or wavelengths of light pass or transmit through the sample when a broadband light source is directed at a sample. In one aspect of this embodiment, a sample is present within a droplet. In another aspect, a sample is present within or coated on a discrete particle. In one example, the discrete particle is a cell. In another example, the discrete particle is a bead. In another aspect, a sample is present within a single-phase flow.

Referring now to FIG. 1, which is an illustration of one embodiment of a system constructed in accordance with the present invention. The system is designated generally by the reference numeral 1-100 and referred to as the "system" or "detection system" and wherein both terms are used interchangeably in this example and throughout other examples discussed below. The system 1-100 provides an instrument for performing detection and measurement of spectroscopic properties of a sample of interest. The application of system 1-100 in FIG. 1 for detection and measurement of fluorescence in droplets comprising a fluorescently-labeled sample in an emulsion is described for exemplary purposes only, as the system 1-100 may be used for the detection and measurement of other spectroscopic properties (e.g., chemiluminescence, scattered light, or transmitted light) of other types of samples as described previously and below.

The system 1-100 comprises a microfluidic housing 200 comprising one or more microfluidic devices 202 continuous with a microfluidic channel 203. The sample of interest, which in this example is an emulsion comprising droplets containing fluorescently-labeled sample, is introduced into the microfluidic devices 202 and flows through the one or more microfluidic devices 202 into the microfluidic channel 203. In alternative embodiments of the system 1-100 illustrated in FIG. 1, as well as systems described in other examples, the sample may be present within or coated on a discrete particle (e.g., a cell or a bead), or may be present as a single-phase flow as described previously and below.

The microfluidic channel 203 of the present embodiment is encased as necessary in an optically clear material to allow for optical excitation and detection and measurement of fluorescence. In alternative embodiments of system 1-100 in illustrated in FIG. 1, as well as systems described in other examples below, the microfluidic channel 203 may be encased in optically clear material as necessary to allow for appropriate illumination and observation for the detection and measurement of other spectroscopic properties (e.g., chemiluminescence, scattered light, or transmitted light) of a sample of interest flowing through the microfluidic channel 203, as described previously and below. In this example illustrated in FIG. 1, the droplets flowing through the microfluidic channel 203 intersect with a detection area 201, wherein the samples are detected and analyzed by one or more optical elements of the system, described in further detail herein.

Alternative embodiments of the system according to the present invention may further comprise one or more microfluidic devices, each continuous with more than one microfluidic channel, wherein multiple samples are introduced into the detection area via the multiple microfluidic channels. In such embodiments, the entire microfluidic device is illuminated as necessary by one or more light sources, described in further detail herein, resulting in excitation or illumination of many samples in several detection areas simultaneously in several microfluidic channels.

The system 1-100 of FIG. 1 further includes a light source 101 for excitation or illumination as necessary of the sample of interest. The light source 101 used in any embodiments of the present invention may include but is not limited to lasers, light-emitting diodes (LEDs), arc lamps, and high intensity light bulbs. One of skill in the art will appreciate the various light sources available from commercial vendors and utilized in the present invention. One of skill in the art will further appreciate that arc lamps and high intensity light bulbs further require accompanying filters to block out detection wavelengths, described in further detail herein.

The light source 101 emits a beam of light 105 having characteristic spectral content. The beam of light 105 is directed by mirrors 102 and 103 and focused by lens 104 to create an illuminated area coincident with the detection area 201, exciting fluorescence (in this example) in the sample-containing droplets as the droplets intersect with the detection area 201 while flowing through the microfluidic channel 203. Alternatively, the beam of light 105 may be introduced co-axially through the objective optic 401. In any case, the fluorescently-labeled sample (in this example) emits fluorescent light in any and all directions that has a wavelength generally greater than that of the light source 101. The emitted spectrum of fluorescence may encompass wavelengths including and below the excitation wavelength, however, such regions of the fluorescence spectrum are rarely detectable as a practical matter.

In alternative embodiments of the system 1-100 illustrated in FIG. 1 and other examples described below, the beam of light emitted by the light source and directed and focused by the components described herein may be used to cause illumination of a sample or selective absorption of light in a sample, resulting in scattered light or transmitted light from the sample, as described previously and below. In additional alternative embodiments wherein the sample of interest contains chemiluminescent substances, which emit light as a result of chemical reactions within the sample and without any excitation by an external light source, detection and measurement of the spectroscopic properties of such a sample may be made in the same way as in the system 1-100 of FIG. 1, but without the need for an excitation light source illustrated by components 101 through 104, which may be removed in such instances.

The objective optic 401 collects the downwardly-oriented portion of any light leaving the sample of interest and collimates the light into a beam of quasi-parallel or substantially parallel rays, referred to herein as a beam of collimated light 450. The objective optic 401 may be selected, for example, from commercially available optics from vendors such as Olympus, Nikon and Kowa Optimed, Inc. While the UPL-SAPO series lenses from Olympus or the CFI series lenses from Nikon are preferred examples of objective optics, one of skill in the art will appreciate the applicability of commercially available or customized/special-order optics that may be used as the objective optic 401.

The resulting beam of collimated light, in the form of an emission beam 450, passes through a filter 402. The filter 402 removes a substantial portion or practically all of the excitation light from the emission beam 450. In one example of this embodiment, the filter 402 is a notch filter, which filters out light having essentially the wavelength of the light source 101 while allowing substantially all other light to remain for detection and measurement, including the light emitted by a fluorescently-labeled sample (or light from a sample in the form of chemiluminescence, scattered light, or transmitted light as in other embodiments described herein).

In another example of this embodiment, the filter 402 is a long pass filter, which filters out light having a wavelength of essentially that of the light source 101 and light of substantially all wavelengths less than that of the light source 101, allowing essentially only light having a wavelength approximately greater than that of the light source 101, which may include the light emitted by a fluorescently-labeled sample (or light from the sample in the form of chemiluminescence, scattered light, or transmitted light as in other embodiments described herein), to remain for detection and measurement.

The filter 402 may also be placed in different locations, such as between the objective optic 401 and the microfluidic housing 200 or between the dispersive element 403 and the camera lens 404. Components 401-404 are referred to collectively herein as the "optical train" 420. In any embodiment, the filter 402 will have essentially the same effect of blocking or rejecting all or a substantial portion of the excitation light of the light source 101, effectively preventing the excitation light from arriving at the image sensor 501. However, because the resulting image (to be discussed further herein) is spectrally dispersed, a relatively modest amount of excitation light reaching the image sensor is not necessarily problematic and may be used advantageously for wavelength calibration, as will be known and appreciated by one of skill in the art. Accordingly, the blocking or rejection quality of the filter 402 need not be particularly high.

After passing through the filter 402, the light then passes through a dispersive element 403, which angularly disperses the light according to the constituent colors of the light, represented in FIG. 1 in the form of dispersed rays 452. The dispersive element 403 may be, for example, a dispersive prism as illustrated in FIG. 1 or, alternatively, a diffraction grating such as a plane transmission grating or a plane reflection grating that may include but is not limited to a grating comprising ruled or holographic, replicated, or volume type fabrication. The dispersive element 403 may also be a zero-deviation (also referred to as "direct view") prism device, as described in U.S. Pat. No. 5,862,001, which is incorporated herein by reference in its entirety. Other dispersive (optical) elements may be used, as will be apparent to and appreciated by those skilled in the art. The dispersed rays 452 are captured by a camera lens 404, which focuses the resulting dispersed light 451 onto an image sensor 501. In one embodiment, the camera lens 404 is selected from the JC10M series, including the LM35JC10M 35 mm focal length lens, commercially available from Kowa Optimed, Inc. One of skill in the art will appreciate the commercially available and custom-designed products that may be used as the camera lens 404. It will be appreciated to those skilled in the art that the optical train 420 described above using refractive optics (lenses) may equivalently be implemented in whole or in part using reflective optics (mirrors), with substantially the same functionality.

In an alternative embodiment, dispersed images at the image sensor 501 may be obtained, without the dispersing element 403, by employing an anamorphic optic, such as a cylindrical lens, at a location approximate to and in place of a dispersing element 403, and placing a linear variable bandpass interference filter (LVF) in contact with, or in close proximity to, the image sensor 501. The anamorphic optic may be oriented so as to spread an elongated image of the sample along the dispersion axis 502 of the sensor 501, and the LVF may be positioned along the elongated image with its wavelength transmission gradient oriented along the dispersion axis 502. This alternative embodiment, while feasible, is less preferred over other embodiments due to its relative inefficiency as only a small fraction of the total light emitted from a sample is actually detected, with the out-of-band light at each point along the elongated image being reflected by the LVF and lost. One of skill in the art will know and appreciate suitable LVF devices and coatings available for use in the present invention including, for example, devices and coatings commercially available from JDS Uniphase Corporation of Milpitas Calif. and Research Electro Optics, Inc. of Boulder Colo., and many other vendors. LVF technology, including the fabrication of LVF filters directly upon an array sensor, is described in U.S. Pat. No. 5,159,199, which is incorporated herein by reference in its entirety.

The image sensor 501 is disposed to capture an image of the dispersed light 451 from a sample present in the detection area 201. Because the dispersed light 451 has been separated spatially in accordance with the constituent colors of light encompassed therein, the image sensor 501 needs to be sensitive only to the spatial distribution and intensity of the incident light, and does not need to discern its color content. The image sensor 501 may be incorporated into a camera, providing a light-tight housing and electronics for controlling the sensor and digitizing the output for analysis, such as depicted in FIG. 1 as the image camera 500.

If the spectral spread of the dispersed images captured at the image sensor 501 is relatively large compared to the size of the images themselves and the color content of the detected light generally comprises substantially discrete wavelengths, then multiple distinct images of the sample will be substantially discretely detected along the axis 502 of the image sensor 501. As spectral spread of the image at the image sensor 501 decreases, discrete wavelength images will begin to overlap. Additionally, typical dyes employed for fluorescent labeling do not have discrete wavelength emissions but, rather, have characteristic emission spectra spread across a range of wavelengths. Spectroscopic properties of interest in types of samples other than fluorescent samples may also be characterized by spectral signatures spread out over a range of wavelengths. Moreover, in examples where the set of spectral signatures being simultaneously detected overlap, their respective images produced by the camera lens 404 will overlap. However, the images produced can be separated by mathematical decomponenting further described herein.

The image detected by the image sensor 501 is based upon the combination of fluorescent dyes (as in the case of a fluorescently-labeled sample in this example) present in the samples in the detection area 201. Thus, the image detected may be a superposition, according to the respective dye concentrations, of the characteristic emission spectra of the fluorescent dyes comprised within a droplet (in this example).

Other spectroscopic properties, such as multiple absorption spectra or multiple chemiluminescent emission spectra may also be detected as a superposition of the sample's individual constituents' effects. Accordingly, mathematical decomponenting may be used to determine the identity and concentration of multiple constituents within the sample based upon the image captured by the image sensor 501, as for determining the identity and concentration of each fluorescent dye present in a droplet. As will be appreciated by one of skill in the art, the process of mathematical decomponenting for the signal of a fluorescently-labeled sample involves taking the image captured by the image sensor 501, together with a known set of characteristic fluorescence emission spectra, and determining a combination of intensities of the known emission spectra which, when superimposed, would produce the image captured by the image sensor 501. Those skilled in the art will know and appreciate the range of mathematical techniques, including linear regression, which may be used to accomplish this decomponenting appropriate for the particular dyes being used.

In one embodiment, samples of interest (e.g., droplets containing fluorescently-labeled sample as in this example) flow past the detection area 201 in a direction that is approximately perpendicular to the direction along which the emission beam 450 is dispersed at the dispersive optic 403. When employing this arrangement, an instantaneous signal of each sample is produced at the image sensor 501 in the form of one or more images of varying intensities distributed along the image sensor axis 502 at various positions determined by the particular wavelengths of light emitted by the sample. The image positions along the direction of the image sensor axis 502 are a function only of the spectral content of the emitted light. With respect to the motion of the droplet in the microfluidic channel 203, the set of dispersed images also moves commensurately across the image plane, in a direction perpendicular to the sensor axis 502. Thus, observations of moving droplets taken along a single line in the plane of the image sensor 501 parallel to sensor axis 502 will be in the form of pulses of varying fluorescent intensities distributed along the line. Further, a relationship may be established at the image sensor 501 relating the emitted wavelength at the detection area 201 and the position of an observed image produced at the image sensor 501 along the line of observation that does not change with time and is independent of the motion of a particular sample.

In an alternative embodiment, droplets or other samples of interest flow past the detection area 201 in one or more microfluidic channels 203 oriented at any other angle from that shown in FIG. 1, including substantially parallel or substantially orthogonal angles, relative to the direction along which the emission beam 450 is dispersed at the dispersive optic 401. In this embodiment, the variation of fluorescent intensity of emitted light that is measured in a particular location represents a convolution of both the motion of the droplet or other sample of interest in the detection area 201 and the color of light emitted by the fluorescently-labeled sample in a droplet (or the color of light from the sample in the form of chemiluminescence, scatter or transmission as in other embodiments described herein).

As described previously, in an alternative embodiment of the system of the invention, the sample of interest is a single-phase flow of fluid in the microfluidic channel 203. Observations of the sample of interest in such an embodiment will be in the form of a continuously detected pattern of intensities at the image sensor 501. If this stream of fluid has spectroscopic properties that vary according to its composition, and its composition varies with time, the pattern of intensities measured at the image sensor 501 will also vary. However, detection and measurement of the spectroscopic properties of single-phase flow samples may be made in substantially the same manner as for droplets in an emulsion as described for the system 1-100 of FIG. 1.

As described previously, in another alternative embodiment of the system of the invention, the sample of interest is a cell or bead, or suspension of cells or beads, flowing in the microfluidic channel 203. Detection and measurement of the spectroscopic properties of such samples may be made in substantially the same manner as for droplets in an emulsion as described for the system 1-100 of FIG. 1.

As described previously, in yet another alternative embodiment of the system of the invention, the sample of interest contains chemiluminescent substances which emit light as a result of internal chemical reactions and without any excitation by an external light source. Measurements of the spectroscopic properties of such a suspension may be made in the same way as in the system 1-100 of FIG. 1, removing the need for an excitation light source illustrated by components 101 through 104.

In yet another alternative embodiment of the system of the invention, the sample of interest does not flow but, rather, the detection system itself moves with respect to the sample, so as to create a relative motion between the detector and sample, and measurements may be made of spectroscopic properties of the sample in the same way already described.

In an alternative embodiment of the system of the invention, the sample of interest is not fluorescent, but reflects characteristic colors of incident light in the form of scattered light. In such a system, the light source 101 would be a broadband source, and the sample in the detection area 201 would reflect only certain colors of the incident beam of light 105 that would be detected in the same way as for the system 1-100 of FIG. 1 at the image sensor 501.

In an alternative embodiment of the system of the invention, the sample of interest absorbs characteristic wavelengths of light. In such a system, the light source would be a broadband source, emitting an extended range of wavelengths (e.g. in the near infrared, visible, or ultraviolet spectral regions). This light source may be, for example, a white light LED, a tungsten incandescent lamp, or an arc lamp. It would be positioned on the axis of objective lens, with the incident beam of light coincident with said axis, above the sample of interest, such that only light not absorbed (i.e., light that is transmitted) by the sample would be detected in the same way as for the system 1-100 of FIG. 1 at the image sensor 501.

Figure 2B:
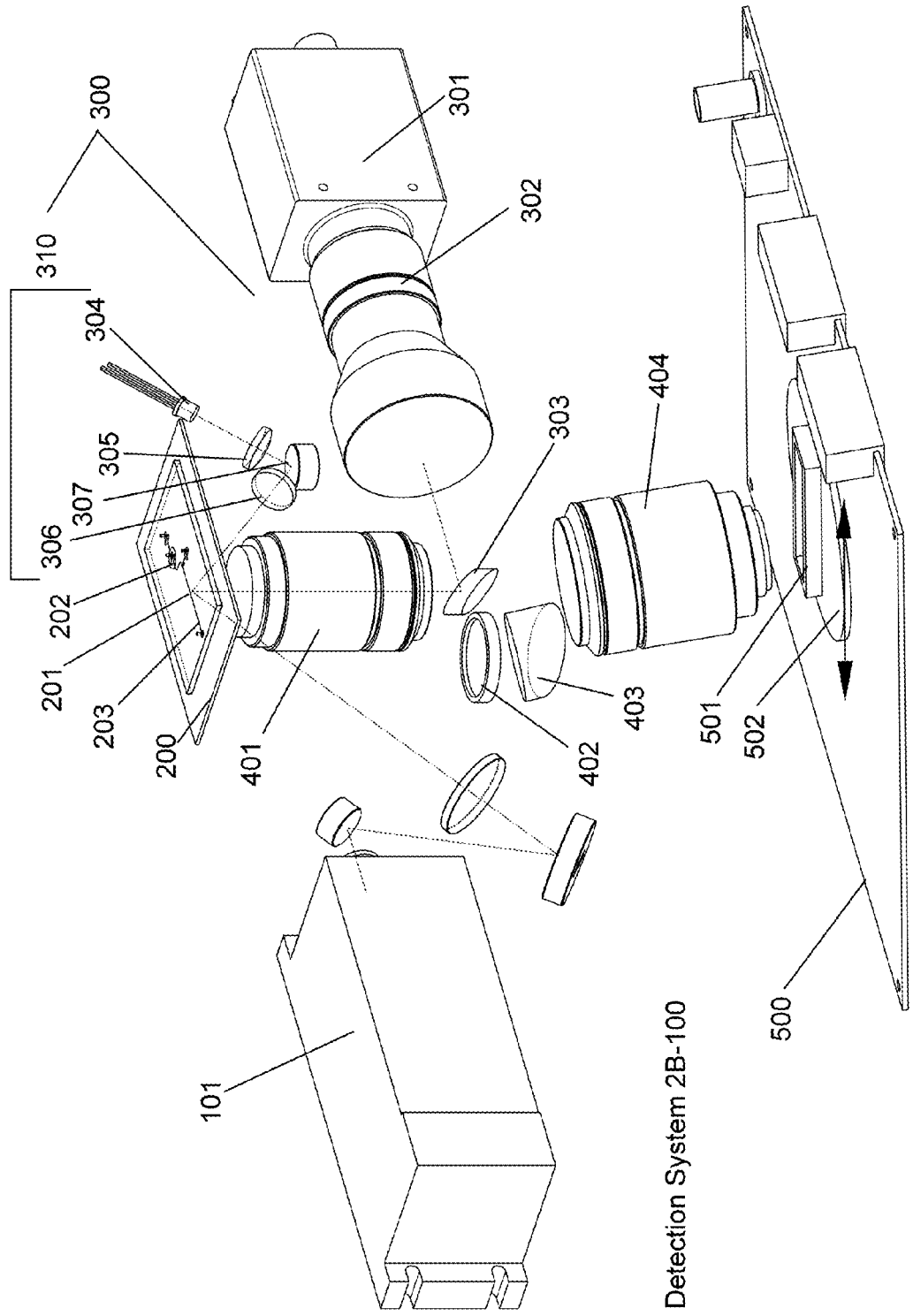
FIG. 2B is a representative illustration of a monitor camera system adapted to the system of FIG. 1, employing epi-illumination of the sample.

Referring now to FIGS. 2A and 2B, which illustrate alternative embodiments of the system of the invention (referred to as Detection System 2A-100 and 2B-100 in FIGS. 2A and 2B, respectively), incorporating the use of a monitor camera system 300 for visually observing the microfluidic channel 203 and the sample(s) flowing therein. The monitor camera system 300 is utilized primarily for diagnostic and calibration purposes, such as during alignment of the optical components of the detection systems 2A-100 and 2B-100, to provide an ordinary undispersed plane image view of the samples at the detection area 201, all of which will be understood and appreciated by one of skill in the art. The monitor camera system 300 comprises a monitor camera 301 equipped with a monitor camera lens 302. In one embodiment, when the monitor camera system 300 is in use, components of the optical train 420 between the lenses 401 and 404 illustrated in FIG. 1 and in previously described embodiments herein, are moved out of position as necessary, and a fold mirror 303 is moved into position allowing it to reflect undispersed light from the objective optic 401 into the monitor camera 301. To accomplish this, the dispersive optic 403 and fold mirror 303 may be located on a mechanism, such as a rotating wheel or a carriage constrained to travel on a linear rail, that allows either the dispersive optic 403 or the fold mirror 303 to be moved into the appropriate position, allowing the user to switch manually between operation and monitor modes.

When using the monitor camera system 300, the light directed into the monitor camera 301 does not pass through the dispersive element 403. This allows for chromatically unsmeared images of the sample present in the microfluidic channel to be observed, in either a static or dynamic mode. Where the light used for detection coming from the sample, which may comprise excitation, illumination, or light originating within the sample itself, is not adequate for obtaining a useful view of the microfluidic channel 203, the monitor camera system 300 further comprises a separate monitor light source system 310, which illuminates the detection area 201 instead of, or in addition to, the light from the detection systems 2A-100 and 2B-100 when the monitor camera system 300 is in use. The image in the monitor camera 301 will be made up of light scattered in the detection area 201 from both the droplets containing fluorescently-labeled sample (or light from other samples or in the form of scattered light, transmitted light, or chemiluminescence, as in other embodiments), as well from the material encasing the microfluidic channel 203.

FIG. 2A illustrates one aspect of an embodiment comprising a monitor camera system 300 depicting a monitor light source system 310 that, in this example, illuminates the sample by means of a monitor light source 304, a monitor light source relay lens 305 and a monitor light source focus lens 306. These components 304-306 of the monitor light source system 310 are arranged coaxially with the objective optic 401 and above the microfluidic housing 200, so as to illuminate the detection area 201 from behind. This is referred to as "trans-illumination".

FIG. 2B illustrates an alternative aspect of an embodiment comprising a monitor camera system 300, wherein the monitor light source system 310 additionally comprises a monitor light fold mirror 307. In one example of the aspect illustrated in FIG. 2B, the monitor light source 304 comprises a visible LED, which is imaged via lenses 305 and 306 and fold mirror 307 onto the region of the microfluidic device encompassing the detection area 201 to provide a light source for the monitor camera 301. This is referred to as "epi-illumination".

It will be appreciated by those skilled in the art that many alternate configurations of the components of the monitor light source system 310 may also be employed. For example, configurations employing various alternative monitor light sources to serve as the monitor light source 304, including but not limited to incandescent or visible LED sources, and various optical elements including but not limited to a single relay lens or a focusing mirror, or configurations employing no additional optics, may allow the monitor light source 304 to illuminate the detection area more directly.

In one aspect of the embodiments incorporating a monitor camera system 300, where the sample comprises rapidly moving droplets or discrete particles, the monitor light source 304 may optionally be strobed at the droplet or particle arrival rate to permit the imaging of the rapidly streaming droplets or particles. This may be accomplished by using monitor cameras having relatively modest frame rates and relatively long exposure times, such that unstrobed droplet or particle images would be severely smeared by droplet motion. In an alternative aspect, a beam splitter (e.g., a dichroic beamsplitter), may be used for monitoring purposes in lieu of the fold mirror 303 by being placed, for example, below the filter 402 and above the dispersive optic 403.

The image sensor of the system of the invention may be comprised of a single monochrome light sensor, sensitive to any color of light across the entire range to be detected, or a pixel array of light sensors in one dimension (a line) or two dimensions (a grid). The image sensor may be selected, for example, from a charge coupled device (CCD), a complementary metal-oxide-semiconductor (CMOS) (alternatively referred to as a complementary-symmetry metal-oxide-semiconductor (COS-MOS)), one or more individual photodiodes, photodiode arrays (PDAs), avalanche photodiodes (APDs), avalanche photodiode arrays, photomultiplier tubes (PMTs), or photomultiplier tube arrays. The number and placement of individual sensor elements will determine the spectral bandwidth and resolution for detection with the system, with preferred embodiments incorporating array sensors for arbitrary spectral detection. One dimensional CCD or CMOS arrays are often referred to as Line Scan devices. In the case of two dimensional CCD or CMOS arrays, the sensor may be of either the Area type or Time Delay Integration (TDI) type. In examples where the image sensor is an array type image sensor, the color content of the detected light is determined by correlating the known spectral spread caused by the dispersive optic with the particular areas of the image sensor that are detecting an image. If the spectral spread is large compared to the size of the image of the sample, multiple distinct images of the sample will be made on the image sensor, which can be discretely detected. The image sensor readout rate i.e., the rate at which the image sensor captures images, must be sufficient to accommodate the droplet arrival rate and velocity at the detection area.

Each type of image sensor described thus far may be incorporated into a camera, providing a light-tight housing and electronics for controlling the sensor and digitizing the output for analysis, such as depicted in FIG. 1 as the image camera 500. In the case of two-dimensional Area cameras, the output is a series of two-dimensional image frames. For Line Scan and TDI cameras, the output may be essentially a continuous stream of 1-D lines, which may be depicted as a continuous record with dispersed droplet spectra on the line axis and time on the continuous axis. One of skill in the art will appreciate the features of Area, Line Scan, and TDI-type image sensors and cameras, which are further described in U.S. Patent Application Publication No. 20050237403 and U.S. Pat. No. 5,434,629, each of which is incorporated herein by reference in its entirety.

In an alternative embodiment, a TDI-type method of image acquisition may be employed as the image sensor. In this embodiment, a TDI camera is employed having a TDI image sensor incorporated therein. The TDI image sensor is a two-dimensional semiconductor light sensor chip (e.g., CCD or CMOS). The TDI camera interfaces the TDI image sensor to the real world. The sensor in the TDI camera comprises multiple adjacent rows of pixels. The pixels are light-sensitive charge wells in which electrical charge accumulates as a result of light incident on each pixel. The TDI camera transfers the charges collected in each row of pixels to an adjacent row of pixels at a regular, programmable rate. The process by which the TDI camera transfers pixel charge from row to row for eventual readout at the final row of the sensor is referred to as "line transfer" and the rate at which this transfer occurs is the "line transfer rate". The first row in the chain begins with no charge, and at the last row the total amount of charge accumulated in each pixel is read out as a one-dimensional image. The image is essentially a superposition of a series of exposures taken in each row of the TDI camera sensor during the successive periods of time during which charges were moved across all the rows of the sensor. In the TDI camera's normal mode of operation, the charge transfer from each row to the next, accompanied with the reading out of a row of accumulated charges from the last row of pixels, is done at a relatively constant, yet adjustable, line transfer rate. It should be noted that best use of a TDI camera requires a relative motion of the observed droplet relative to the camera that is synchronized to the line transfer rate such that the series of exposures superposed is of substantially the same subject, a requirement that is described in U.S. Patent Application Publication No. 20050237403 and U.S. Pat. No. 5,434,629, each of which is incorporated herein by reference in its entirety.

In embodiments of the invention employing a TDI camera, one-dimensional images may be collected with effective exposure times that are substantially greater (e.g., by a factor of the number of rows on the image sensor) than the line transfer rate-driven interval between successive reads from the sensor. The number of rows on the TDI sensor over which the image of the entire illuminated detection area extends will determine the factor by which the effective exposure time to a subject moving through the detection area may be increased. However, when the width of the image of the illuminated detection zone approaches the width of a single TDI sensor pixel row, this advantage is lost and the performance of a TDI camera becomes similar to that of a Line Scan camera. Accordingly, with appropriate illumination optics, embodiments employing Line Scan cameras are highly feasible. In the discussion below, it will be appreciated that Line Scan embodiments are effectively equivalent to single-line TDI embodiments.

Figure 3:
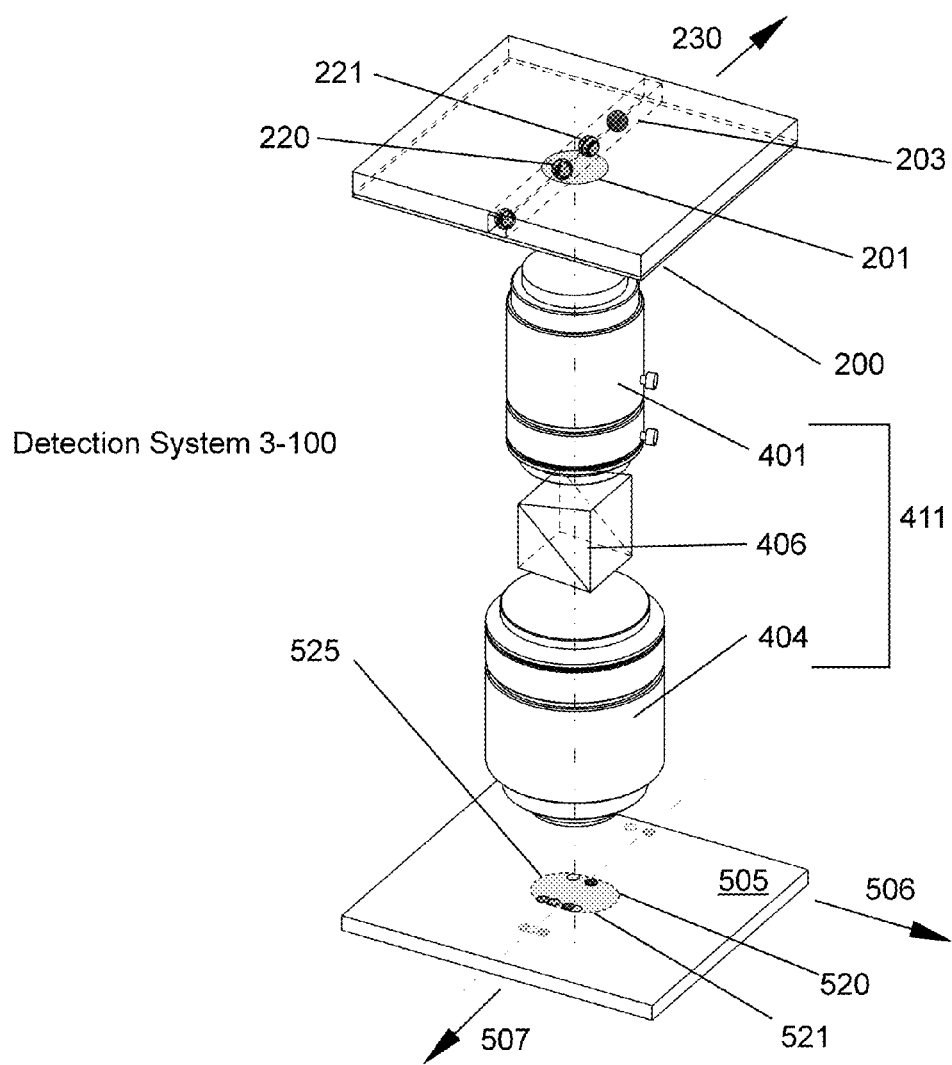
FIG. 3 is a schematic illustration of the dispersed images produced by one embodiment of the present invention.

Referring now to FIG. 3, which illustrates a system 3-100 comprising a microfluidic housing 200 comprising at least one microfluidic channel 203 disposed substantially perpendicular to the optic axis of objective lens 401. FIG. 3 illustrates an embodiment of a system for detection and measurement of droplets comprising fluorescently-labeled samples but may be adapted to the detection and measurement of any sample or spectroscopic property described previously and below. The dispersion axis 506 is perpendicular to both the microfluidic channel 203 and the optic axis of objective lens 401. The samples are illustrated as droplets 220 and 221, each with spectroscopic properties to be detected and measured, in this case the fluorescence produced by different concentrations of fluorophores present in the droplets 220 and 221, which flow or stream in the indicated flow direction 230 through the microfluidic channel 203. Different and particular labels are indicated schematically by the different surface patterns of the droplets 220 and 221 in FIG. 3. A portion of the microfluidic channel 203 is illuminated by an excitation light source (not depicted in FIG. 3) to form the detection area 201.

In the example illustrated in FIG. 3, fluorescent light emitted from the fluorescently-labeled sample in the streaming droplets 220 and 221 is imaged by the optical train 411 onto an image plane 505. In this embodiment, the dispersing element 406 is a zero deviation (also call "direct view") device such that the camera lens 404 may be disposed coaxially with the objective lens 401. The region of the image plane occupied by the dispersed image of the entire detection area 201 for the spectral range being detected is depicted by image extent 525. The inverted droplet images 520 and 521, corresponding to droplets 220 and 221 respectively, are dispersed along a dispersion axis 506 and move in the direction of the image motion vector 507, parallel but opposite to the flow direction 230 of the droplets within the microfluidic channel 203. FIG. 3 shows the images at one instant in time. Only those droplets lying within the illuminated portion of the detection area 201 generate an image. Each such image consists of spectral peaks corresponding to each of the fluorophores present in the corresponding droplet, with intensities related to the concentrations of these fluorophores.

Figure 4A:
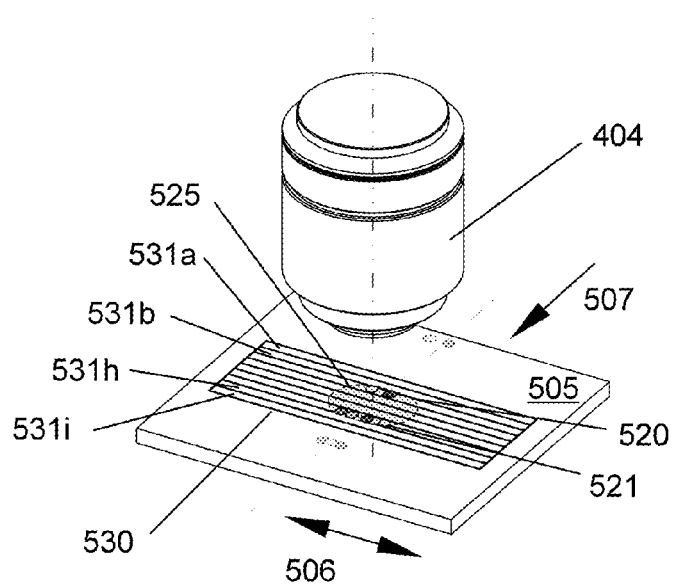
FIGS. 4A and 4B are schematic illustrations of different types of image sensors being used to read the dispersed images produced by the system of FIG. 3.
Figure 4B:
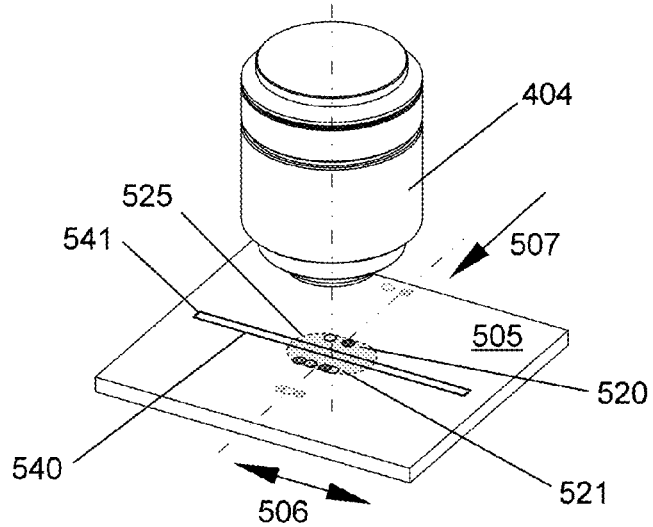

In order to detect the dispersed droplet images 520 and 521, an image sensor is placed in the image plane 505 so as to intercept the image extent 525, examples of which are illustrated in systems 4A-100 and 4B-100 in FIGS. 4A and 4B, respectively. FIGS. 4A and 4B (and subsequent FIG. 4C) illustrate embodiments of a system for detection and measurement of droplets comprising fluorescently-labeled samples of interest but may be adapted to the detection and measurement of any sample or spectroscopic property described previously and below. In FIGS. 4A and 4B, only the final elements of the optical train, i.e. camera lenses 404, are depicted. FIGS. 4A and 4B depict, as examples, the light-sensitive areas in the image plane 505 of two preferred types of sensors. In FIG. 4A, the light-sensitive area 530 of an eight-row TDI sensor is depicted, and in FIG. 4B, the light-sensitive area 540 of a Line Scan sensor is depicted. Each is being read out at substantially identical or similar line rates. The TDI sensor's light-sensitive area is subdivided into eight pixel rows 531a-531h. With each read cycle, the TDI camera, whose light-sensitive area 530 is depicted in FIG. 4A, reads a line out from pixel row 531i and transfers charge from pixel rows 531a-531h (which includes intervening pixel rows not labeled) to pixel rows 531b-531i (which includes intervening pixel rows not labeled). The Line Scan camera, whose light-sensitive area 540 is depicted in FIG. 4B, reads out lines from the sensor's single pixel row 541. In FIG. 4A, the TDI line transfer direction and rate are chosen to ensure synchrony between the TDI camera and the velocity of the droplet images 520 and 521, indicated by the image motion vector 507, as previously discussed. For the Line Scan example of FIG. 4B, synchrony is not required (discussed further below). In each example, the length of the respective image sensor is disposed along the axis of dispersion 506 in the image plane 505.

Figure 4C:
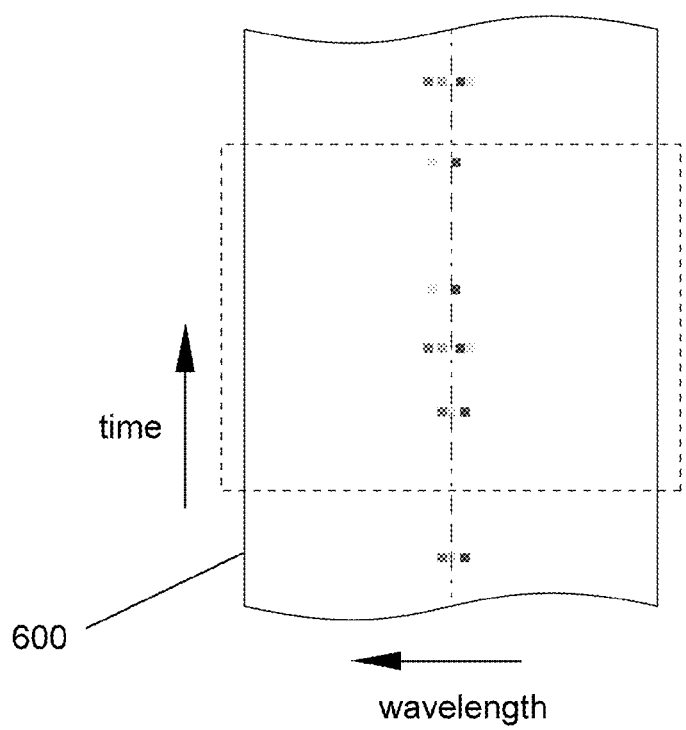
FIG. 4C is an exemplary two dimensional representation of a digitized record of data received from an image sensor, according to aspects of the present invention.

Over time, the lines read out from any image sensor may be depicted in the form of a two dimensional record, an exemplary portion of which is represented in the digitized record 600 of FIG. 4C. As illustrated in FIG. 4C, horizontal rows of the digitized record 600 comprise lines of intensities as read out from the image sensor, and said lines are arranged from bottom to top in the order they were read out. The width of digitized record 600 is limited by the number of pixels in a line of data read out from the image sensor, whereas the height of digitized record 600 is indefinite, limited only by the length of time over which data are collected. From the digitized record 600, the passage of individual samples is readily detected, and the dispersed spectra may be analyzed as previously discussed to determine, in this example, the types and concentrations of fluorophores present in each droplet.

With any image sensor, an appropriate line rate must be chosen so that individual readings from the camera do not include exposure to multiple adjacent droplet images. In examples utilizing TDI methods, this can be accomplished by optimizing the line transfer rate, whether by deriving it from a known droplet velocity or arriving at it empirically by a process of minimizing the smearing in the time axis as seen on a record such as that in FIG. 4C. In examples utilizing a Line Scan image sensor, this line rate optimization is not required, however, the line rate must be sufficient to accommodate droplet image motion across the single pixel row with each sample being detected in at least one, and typically several, consecutive readouts, and with at least one readout between droplets substantially devoid of signal. Alternate embodiments to those depicted in FIGS. 4A and 4B that incorporate an Area sensor in place of the TDI sensor or Line Scan sensor, respectively, must employ frame rates sufficiently high to avoid droplet overlap in the captured images.

In several alternative embodiments of the system of the invention, a sample with spectroscopic properties to be measured may be something other than a droplet comprising a fluorescently-labeled sample. Examples already described include samples comprising single-phase flows, a bead or cell or a suspension of beads or cells, and with the light to be detected being scattered, transmitted, or chemiluminescently emitted from the sample. The systems 4A-100 and 4B-100 depicted in FIGS. 4A and 4B, respectively, will create images of the light coming from any such samples in the same way as for the droplets comprising fluorescently-labeled samples illustrated by way of example in these figures.

The embodiments of the system of the invention described thus far can detect any color of light coming from the sample of interest for which the image sensor is sensitive, and can discern any number of different colors, subject to the relationship between the spectral spread created by the optical train and the size of the image sensor's pixels, by employing one optic train and one image sensor. However, the system is limited by the speed at which images of sufficiently high Signal to Noise ratio can be made from the available light on the image sensor, and it may also be limited by the rate at which samples flow or stream through the microfluidic channel.

Detection throughput can be increased with parallel systems, e.g., through the use of multiple microfluidic channels, through which several streams of flowing samples are each directed through one of several detection areas. If the spectral spread associated with a first microfluidic channel does not take up the entire field of view of the optics or the entire length of the image sensor, additional streams of flowing samples may be analyzed through the use of a second microfluidic channel or even multiple microfluidic channels without adding additional image sensors or optic trains to the system. These additional streams of flowing samples may enter the several detection areas and each may be imaged onto several otherwise unused areas of the image sensor. An unlimited number of additional microfluidic channels may be employed in the system, so long as each image detected extends over a sufficient number of pixels on the image sensor to provide the required ability to resolve different colors. For example, each microfluidic channel may require approximately 50-100 pixels along the dispersion axis. Accordingly, a Line Scan sensor with 2048 pixels or a 2-D Area sensor with one dimension of 2048 pixels may accommodate approximately 20-40 microfluidic channels, provided that the entire array of pixels can be read out sufficiently rapidly, and further provided that the optical field sizes of the lenses employed can accommodate the full length of the image sensor. Thus, multiple microfluidic channels may be utilized in the system according to the present invention without adding new optical or detection components. This has beneficial effects for total system throughput, cost and size.

Figure 5:
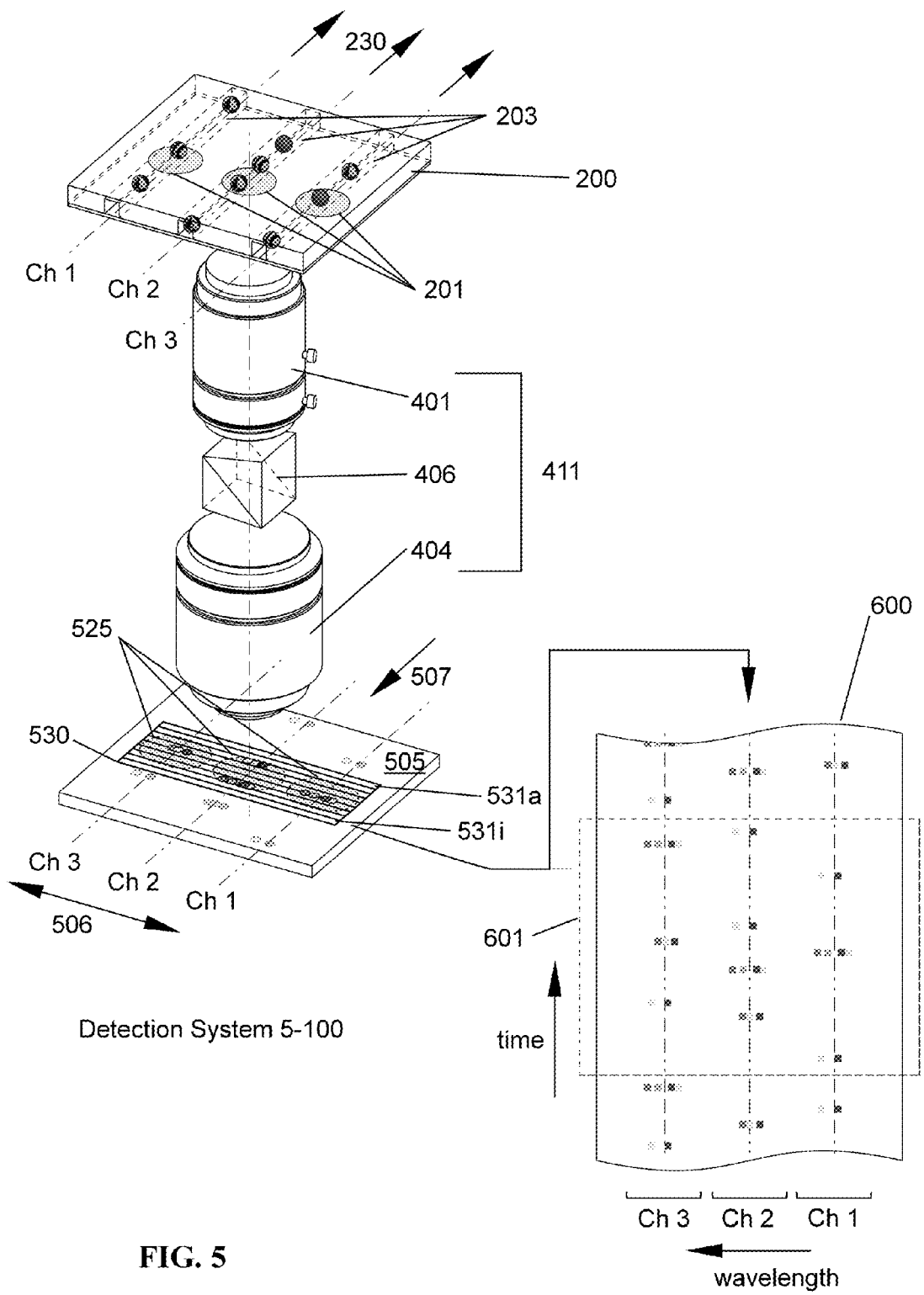
FIG. 5 is a schematic illustration of an embodiment of the system of the present invention employing multiple microfluidic channels and a single image sensor.

Referring now to FIG. 5, which represents an embodiment of the system according to the present invention employing three parallel microfluidic channels labeled Ch 1, Ch 2 and Ch 3 and collectively encompassed by 203, each carrying fluorescently-labeled droplets in an emulsion, and again depicts the light-sensitive areas of a TDI camera's sensor 530 subdivided into pixel rows 531a-531i. FIG. 5 illustrates an embodiment of a system 5-100 for detection and measurement of droplets comprising fluorescently-labeled samples of interest but may be adapted to the detection and measurement of any sample or spectroscopic property described previously. Three microfluidic channels are shown in this embodiment but, as discussed above, fewer or many more microfluidic channels may be used.

The components and operation of the system 5-100 illustrated in FIG. 5 are essentially the same as in the system 3-100 of FIG. 3 and systems 4A-100 and 4B-100 of FIGS. 4A-4B, respectively, except that the digitized record 600 now contains information for droplets in all of the parallel microfluidic channels 203 in each horizontal row, with each microfluidic channel occupying a distinct range of pixels of the TDI line output. The portion of the digitized record corresponding to the images seen in the adjacent illustration of the image plane 505 is indicated by the box 601. In FIG. 5, the illumination has been confined to a relatively small set of detection areas 201, one in each microfluidic channel. Structured illumination of this type may be accomplished by a variety of means, with the specific means depending upon the type of light source employed, all of which will be understood and appreciated by one of skill in the art. For example, with a laser source, engineered diffractive optical elements or holographic elements can be used to split a single beam efficiently into many sub-beams and direct them to the several detection areas. Microlens arrays or aperture masks may also be employed, both for laser sources and non-coherent sources. It is also possible to arrange the illumination optics to form a continuous band of illumination across the microfluidic device, along an axis perpendicular to the axes of the microfluidic channels. Although less energy efficient, this approach can eliminate the need for precise alignment of the illumination spots to the microfluidic channels.

The present invention also pertains to a method for the detection and measurement of spectroscopic properties of light from a sample, or the scalable detection and measurement of spectroscopic properties of light from each sample present among multiple samples, simultaneously, wherein the method comprises the system described above. The light detected and measured comprises light scattered from a sample following illumination of the sample; emitted as chemiluminescence by a chemical process within a sample; selectively absorbed by a sample following direction of a broadband light source at the sample; or emitted as fluorescence from a sample following excitation. Depending on the application, the sample comprises a single-phase flow, the composition of which may vary with time; discrete targets including, but not limited to, beads or cells; or droplets. In one embodiment, the one or more samples of interest are present in an emulsion. In another embodiment, the one or more samples are present in an emulsion within a microfluidic device.

The present invention also pertains to a kit comprising the system described above and the reagents necessary for performing the method described above.

The results of the methods of this invention, referred to herein as "data", associated with a particular sample of interest may then be kept in an accessible database, and may or may not be associated with other data from the particular human, animal, plant or microorganism associated with the particular sample of interest or with data from other humans, animals, plants or microorganisms. Data obtained may be stored in a database that can be integrated or associated with and/or cross-matched to other databases.

The systems, methods and kits of this invention may further be associated with a network interface. The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

Although the present invention and its advantages have been described in detail, it should be understood that various changes, substitutions and alterations can be made herein without departing from the spirit and scope of the invention as defined in the appended claims.

The present invention will be further illustrated in the following Examples, which are provided for illustration purposes only and are not intended to limit the invention in any way.

EXAMPLE

Example 1

Figure 6:
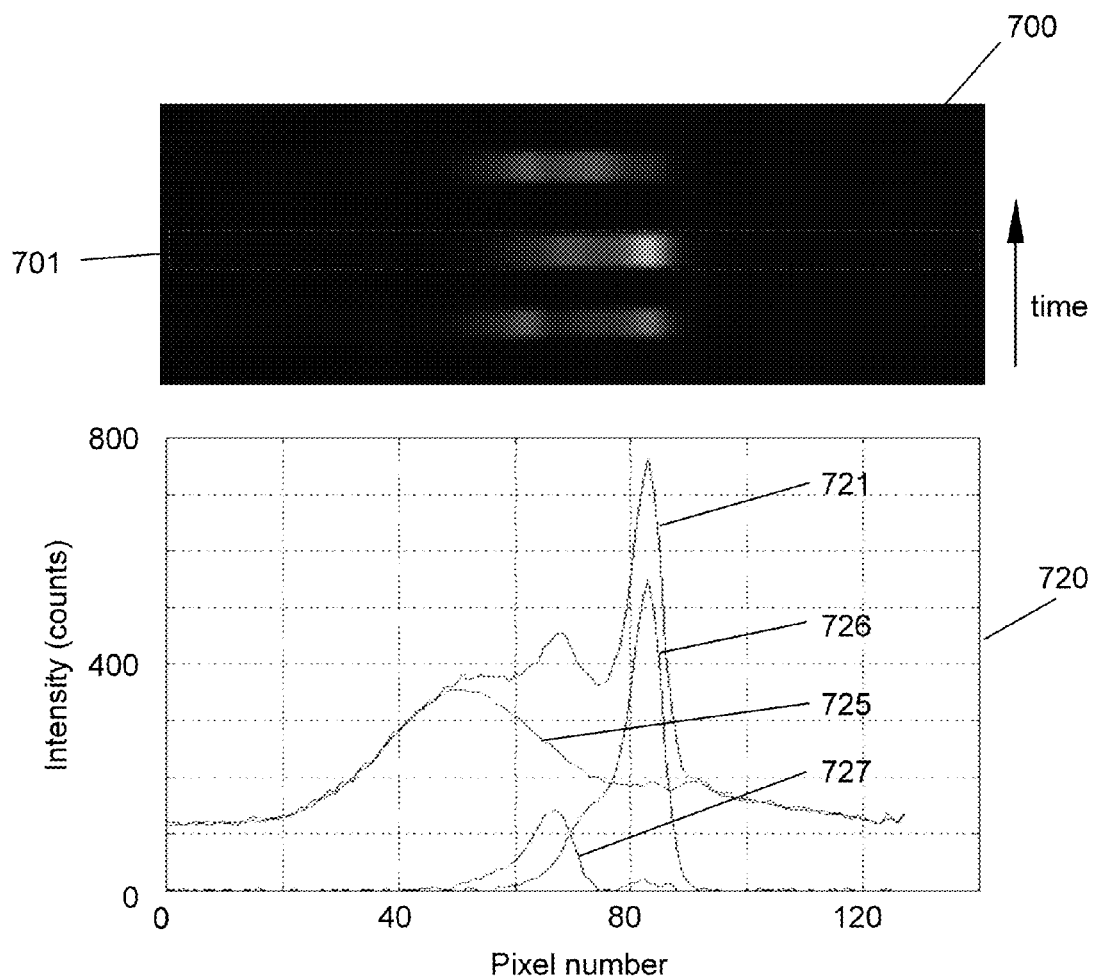
FIG. 6 depicts an example of typical data obtained with droplets as the sample of interest using one embodiment of the system of the present invention and an illustration of the interpretation of the results.

FIG. 6 depicts an example of a reading obtained using an embodiment of a detection system constructed according to the present invention. A portion of a digitized record 700 is shown corresponding to the signal from one particular droplet comprising a fluorescently-labeled sample indicated by the box enclosing droplet signal 701. Detector output comprises lines of pixels of varying intensity, shown in the digitized record 700 as a vertically stacked arrangement with the oldest data at the bottom and the most recent data at the top, with black representing the lowest detected intensity. Below the digitized record 700 is shown a graph 720 representing the results of the mathematical decomponenting of the droplet signal 701. The vertical intensity axis on this graph corresponds directly to the intensity recorded from droplet signal 701, and the horizontal axis corresponds directly to the pixel number in the droplet signal 701. The total signal 721 comprises the following components: an autofluorescence component 725 emitted by the material making up the microfluidic channels upon excitation by incident light; a first fluorescent dye component 726; and a second fluorescent dye component 727. These three components 725-727 may be added to form the total signal 721. The mathematical decomponenting determines an optimally weighted combination of nominal response models for autofluorescence and known dye concentrations, illustrated by curves 725-727, that produces the observed total signal 721. If these nominal response models may be established using observations found within a single run's digitized record 700 and not a separately prepared response model for the response components, then it is not necessary to establish the exact correspondence between pixel number and wavelength.

Example 2

Figure 7:
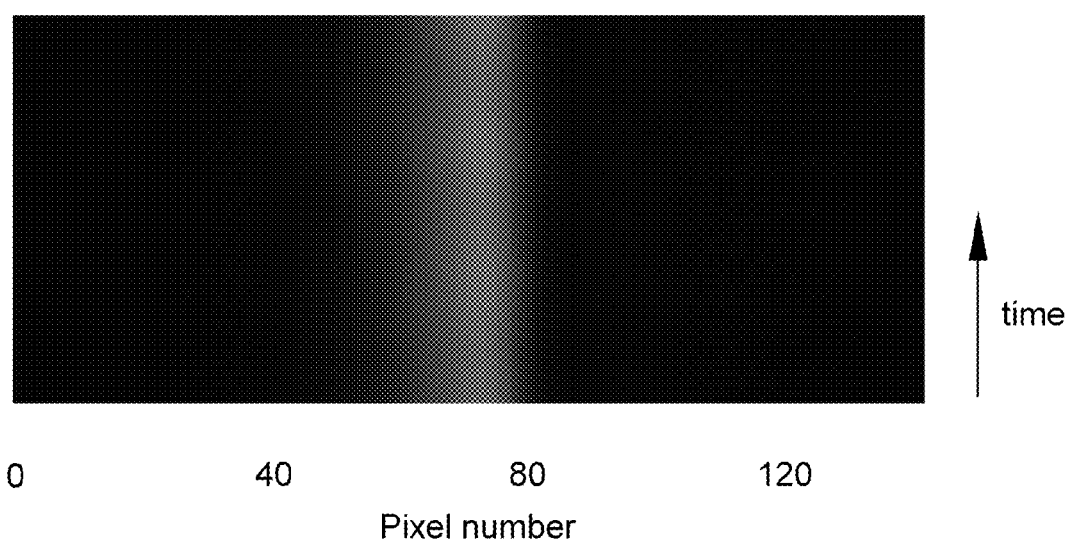
FIG. 7 depicts an example of typical data obtained with a single-phase flow as the sample of interest using one embodiment of the system of the present invention.

FIG. 7 depicts a second example of a digitized record obtained using the same embodiment of a detection system constructed according to the present invention as employed for Example 1. In this instance, the sample of interest is a single-phase flow of a single-dye solution of constant composition. It is seen that the resultant spectral signal recorded is substantially invariant with time.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A system for the detection and measurement of spectroscopic properties of light from a sample, wherein the system comprises:
   a microfluidic housing having a microfluidic channel, the microfluidic channel configured to accommodate a scalable fluid flow of sample;
   an optical train comprising a single dispersing element; and
   an image sensor,
   wherein the light from the fluid flow of sample in the microfluidic channel is spectrally dispersed by the single dispersing element and the spectroscopic properties of light are measured over time on the image sensor as a function of relative motion between the sample and the image sensor, further wherein superimposed measurements of light are mathematically decomponented to determine the identity and concentration of multiple constituents in the sample.

2. A system according to claim 1, wherein the light is selected from the group comprising light scattered from a sample following illumination of a sample, light emitted as chemiluminescence by a chemical process within a sample, light transmitted through a sample as a result of selective absorption of light following direction of a broadband light source at the sample, light emitted as fluorescence following excitation of a sample, and wherein the sample comprises one or more fluorescent label, or a combination thereof.

3. A system according to claim 1, wherein the sample is excited by a light source, wherein the light source is selected from the group comprising: a laser, a light-emitting diode (LED), an arc lamp, a high intensity light bulb, or a combination thereof.

4. A system according to claim 1, wherein the sample comprises either or both of a single-phase flow and a droplet.

5. A system according to claim 1, wherein the sample comprises a discrete target, a discrete target comprising a bead, a discrete target comprising a cell, or a combination thereof.

6. A system according to claim 1, wherein the sample is present within an emulsion.

7. A system according to claim 6, wherein the sample is present within an emulsion within a microfluidic device.

8. A system according to claim 1, wherein the spectroscopic properties of light comprise wavelength and/or intensity.

9. A system according to claim 1, wherein the image sensor is selected from the group comprising: a single monochrome light sensor, a pixel array of light sensors, a pixel array of light sensors in one dimension (a line), a pixel array of light sensors in two dimensions (a grid), a Time Delay Integration (TDI) sensor, or a combination thereof.

10. A system according to claim 9, wherein where the image sensor is a TDI sensor, measurements of light over time are superimposed on the TDI during successive periods of time.

11. A system according to claim 1, wherein the dispersing element is selected from the group comprising: a diffraction grating, a plane transmission grating, a plane reflection grating, a dispersive prism, or a zero-deviation (direct view) prism device.

12. A method for the detection and measurement of spectroscopic properties of light, comprising the system according to claim 1.

13. A kit for performing the method according to claim 12.

14. A system according to claim 1, further comprising a monitor camera system that observes a flow of the sample, having a monitor light source system which illuminates the sample from an epi-illumination position.

15. A system according to claim 14, wherein the sample is excited by the monitor light source system.

16. A system according to claim 1, wherein the monitor camera system is optionally strobed to image rapidly streaming droplets or particles.

17. A system for the scalable detection and measurement of spectroscopic properties of light from each sample present among multiple samples, simultaneously, wherein the system comprises:
   a microfluidic housing having a plurality of microfluidic channels, the microfluidic channels configured to accommodate a fluid flow of sample;
   an optical train comprising a single dispersing element; and
   an image sensor,
   wherein the light from each fluid flow of sample in each microfluidic channel is spectrally dispersed by the single dispersing element and the spectroscopic properties of light are measured over time on the image sensor as a function of relative motion between each particular sample and the image sensor, further wherein superimposed measurements of light are mathematically decomponented to determine the identity and concentration of multiple constituents in the sample.

18. A system according to claim 17, wherein the light is selected from the group comprising light scattered from a sample following illumination of the sample, light emitted as chemiluminescence by a chemical process within a sample, light transmitted through a sample as a result of selective absorption of light following direction of a broadband light source at the sample, light emitted as fluorescence following excitation of a sample, and wherein the sample comprises one or more fluorescent label, or a combination thereof.

19. A system according to claim 17, wherein the sample is excited by a light source, wherein the light source is selected from the group comprising: a laser, a light-emitting diode (LED), an arc lamp, a high intensity light bulb, or a combination thereof.

20. A system according to claim 17, wherein each of the multiple samples comprises either or both of a single-phase flow and a droplet.

21. A system according to claim 17, wherein each of the multiple samples comprises a discrete target, a discrete target comprising a bead, a discrete target comprising a cell, or a combination thereof.

22. A system according to claim 17, wherein the multiple samples are present within an emulsion.

23. A system according to claim 22, wherein the multiple samples are present within an emulsion within a microfluidic device.

24. A system according to claim 17, wherein the spectroscopic properties of light comprise wavelength and/or intensity.

25. A system according to claim 17, wherein the image sensor is selected from the group comprising: a pixel array of light sensors, a pixel array of light sensors in one dimension (a line), a pixel array of light sensors in two dimensions (a grid), a Time Delay Integration (TDI) sensor, or a combination thereof.

26. A system according to claim 25, wherein where the image sensor is a TDI sensor, measurements of light over time are superimposed on the TDI during successive periods of time.

27. A system according to claim 17, wherein the dispersing element is selected from the group comprising: a diffraction grating, a plane transmission grating, a plane reflection grating, a dispersive prism, or a zero-deviation (direct view) prism device.

28. A system according to claim 17, further comprising a monitor camera system that observes each flow of sample, having a monitor light source system which illuminates each sample from an epi-illumination position.

29. A system according to claim 28, wherein the sample is excited by the monitor light source system.

30. A system according to claim 17, wherein the monitor camera system is optionally strobed to image rapidly streaming droplets or particles.

31. A system according to claim 17, wherein each of the multiple samples have an image extent projected onto a separate area of the image sensor.

* * * * *